(12) United States Patent
Chiou et al.

(10) Patent No.: US 9,314,446 B2
(45) Date of Patent: Apr. 19, 2016

(54) SUSTAINED RELEASING PHARMACEUTICAL COMPOSITION

(71) Applicants: Shih-Hwa Chiou, Taipei (TW); Catherine Jui-Ling Liu, Taipei (TW); Yung-Hsin Cheng, Taipei (TW)

(72) Inventors: Shih-Hwa Chiou, Taipei (TW); Catherine Jui-Ling Liu, Taipei (TW); Yung-Hsin Cheng, Taipei (TW)

(*) Notice: Subject to any disclaimer, the term of this patent is extended or adjusted under 35 U.S.C. 154(b) by 0 days.

(21) Appl. No.: 14/275,133

(22) Filed: May 12, 2014

(65) Prior Publication Data
US 2014/0335056 A1 Nov. 13, 2014

Related U.S. Application Data

(60) Provisional application No. 61/821,825, filed on May 10, 2013.

(51) Int. Cl.
| A61K 47/36 | (2006.01) |
| A61K 31/216 | (2006.01) |
| A61K 31/7088 | (2006.01) |
| A61K 9/00 | (2006.01) |
| A61K 31/5575 | (2006.01) |
| A61K 35/00 | (2006.01) |
| A61K 36/00 | (2006.01) |
| A61K 38/00 | (2006.01) |

(52) U.S. Cl.
CPC ............. *A61K 31/216* (2013.01); *A61K 9/0014* (2013.01); *A61K 9/0019* (2013.01); *A61K 9/0048* (2013.01); *A61K 31/5575* (2013.01); *A61K 31/7088* (2013.01); *A61K 35/00* (2013.01); *A61K 36/00* (2013.01); *A61K 38/00* (2013.01)

(58) Field of Classification Search
IPC ................................. A61K 47/36,47/42, 47/02
See application file for complete search history.

(56) References Cited

U.S. PATENT DOCUMENTS

2009/0239875 A1* 9/2009 Chao .......................... 514/252.1

OTHER PUBLICATIONS

Cheng et al., "Thermosensitive chitosan-gelatin-glycerol phosphate hydrogel as a controlled release system of ferulic acid for nucleus pulposus regeneration," Biomaterials 32:6953-6961, 2011.*

* cited by examiner

*Primary Examiner* — Rosanne Kosson
(74) *Attorney, Agent, or Firm* — Birch, Stewart, Kolasch & Birch, LLP (57) ABSTRACT

The present invention relates to a formulation made from a chitosan, a gelatin, and a phosphate salt can provide a sustained release/maintenance of a therapeutic agent, wherein the phosphate salt is selected from the group consisting of disodium phosphate and ammonium hydrogen phosphate.

16 Claims, 7 Drawing Sheets

A

| Time (days) | Cumulative release (µg) |
|---|---|
| 1 | 1.344 ± 0.327 |
| 7 | 26.797 ± 5.401 |
| 14 | 45.026 ± 2.552 |
| 28 | 67.725 ± 4.246 |

| Method | Group | Hemolysis (%) | Hemolysis |
|---|---|---|---|
| | NC | 0.00 | — |
| Direct contact | PC | 11.91 | hemolytic |
| | TA | 0.00 | nonhemolytic |
| | NC | 0.00 | — |
| Indirect contact | PC | 18.37 | hemolytic |
| | TA | 0.35 | nonhemolytic |

SUSTAINED RELEASING PHARMACEUTICAL COMPOSITION

CROSS REFERENCE TO RELATED APPLICATIONS

This patent application claims priority to U.S. provisional patent application Ser. No. 61/821,825 filed on May 10, 2013, which is hereby incorporated by reference in its entirety.

FIELD OF THE INVENTION

The present invention relates to a new approach for sustained releasing a therapeutic agent in a subject through a new composition.

BACKGROUND OF THE INVENTION

Chitosan (CS), a polysaccharide consisting of β-(1,4)-linked glucosamine units, has been extensively investigated for developing hydrogels with unique properties It is known that CS is extracted from fungal cell walls and exoskeletons of arthropods such as crabs, shrimp and krill. It holds several characteristics desirable for biomedical applications, such as: biocompatibility, biodegradation, bioadhesivity, anti-bacterial effects and no toxicity.

In recent years, injectable in situ forming hydrogels are receiving considerable attention for a variety of biomedical applications such as sustained drug delivery, cell encapsulation and scaffolds for tissue engineering (Tae et al., Biomaterials, 26, 5259-5266, 2005). Medical hydrogel has a great advantage including conventional implantation surgery, easy handling by clinic personnel, reducing pain, less complications, reduced healing period, minimal scarring, reduced surgery time, and the ability to conform to irregular defects. Several requirements need to be met for an ideal medical hydrogel, which include: (1) a sol-to-gel transition before and after injection into the sites of injury, (2) a biodegradable or gradually dissolving character, (3) both the hydrogel and the degradation products should be biocompatible, and (4) the gel should present desirable properties for the intended application, for instance, sustained release profile for drug delivery systems, or cell adhesive capabilities for tissue engineering. Recent publications on medical hydrogels highlighted various types of in vivo forming hydrogels, which included thermo-sensitive, pH-sensitive, photo-crosslinked, stereo-complexed, and peptide-based hydrogels. Given the good properties of the CS, hydrogels based on CS were found to be excellent candidates for a variety of medical and pharmaceutical applications (Berger et al., Eur. J. Pharm. Bio. Pharm., 57: 19-34, 2004). Recently, thermo-sensitive hydrogels have received much attention as they can keep liquid form at room temperature but form the hydrogel at body temperature under physiological condition (Cheng et al., Biomaterials, 32: 6953-6961, 2011).

A thermally-responsive composite hydrogel has been developed and synthesized by Bush, which is a chitosan and xylan composite thereto-gelling solution to allow regulating the conditions in which the chitosan and xylan solution will gel. (Bush, U.S. Pat. No. 8,623,403).

It has been proved to use gels for the treatment of diseases of the mucous membranes such as nasal, oral, pharyngeal and urogenital regions, particularly hydrogels, which can be used for protecting mucous membranes as well as for keeping them moist.

However, known gels adhere poorly to the mucous membrane, and cannot maintain them for a sufficient long time in the location to be treated. Further, there is a long-existing problem in the treatment of the diseases in eyes, particularly the therapeutic agent that should be applied to cornea and conjunctiva of an eye. For a pharmaceutical composition for the disease in eyes, it is desirable to last as long as possible in order to keep the eye moist, and to allow the therapeutic agent to act locally. In addition, for a pharmaceutical composition for topical administration in eyes, highly viscous gels should be used but they would pearl off from the mucous membrane of the eyes so that the desired action cannot be achieved.

Consequently, it is still desirable to develop new formulations with better properties for various medical applications, particularly for a delivery through mucous membrane in a subject.

BRIEF SUMMARY OF THE INVENTION

In the present invention, it is unexpected found that a formulation containing a chitosan, a gelatin, and a phosphate salt provides a sustained release or maintenance of a therapeutic agent in the location to be treated in a subject, particularly in mucous membrane. Accordingly, the invention provides a new approach for sustained releasing or maintaining a therapeutic agent contained in a new composition as a delivery system to the location to be treated in a subject.

In one aspect, the invention provides a pharmaceutical composition comprising a therapeutic agent, a chitosan, a gelatin, and a phosphate salt in a solvent at the ratio effective to provide a sustained-release or maintenance of the therapeutic agent in the location to be treated in a subject. In some examples of the invention, the phosphate salt is selected from the group consisting of disodium phosphate and ammonium hydrogen phosphate. In one example of the invention, the phosphate salt is disodium phosphate.

In some examples of the invention, the solvent is selected from the group consisting of dimethyl sulfoxide (DMSO), ethanol, glycerol, glycerol phosphate disodium, polyvinylpyrrolidone (MW 40000), polyvinylpyrrolidone (MW 36000), acetic acid, lactic acid and combination thereof. In one specific example, the solvent is glycerol.

In some examples of the invention, the therapeutic agent is selected from the group consisting of a drug, an antibiotic agent, an anti-metabolic agent, a hormonal agent, a plant-derived agent, cells, stem cells, a vector carrying genetic material, a peptide, and a nucleic acid. In one specific example, the therapeutic agent is a drug.

In some examples of the invention, the pharmaceutical composition may be in the form of an injectable hydrogel, spray, eye drop, ointment, or suppository.

In one further aspect, the invention provides an injectable hydrogen formulation for the administration of a therapeutic agent through a mucous membrane to a location to be treated in a subject, which provides a chitosan, a gelatin, and a phosphate salt in a solvent at the ratio effective to provide a sustained-release or maintenance of the therapeutic agent in the location to be treated.

In the embodiment of the invention, the administration includes but is not limited to oral administration, topical administration, intravenous injection, intracardiac injection, intramuscular injection, intraosseous injection, intraperitoneal injection, intradermal injection, subcutaneous injection, intraocular injection, intracavernous injection, and intra-articular injection. The intraocular injection includes but is not limited to subconjunctival injection, intravitreal injection, or transscleral injection.

In one yet aspect, the invention provides a pharmaceutical composition for treatment or prevention of a disease in eyes, comprising a therapeutic agent, a chitosan, a gelatin, and a phosphate salt in a solvent at the ratio effective to provide a sustained-release or maintenance of the therapeutic agent. In some examples of the invention, the phosphate salt is selected from the group consisting of disodium phosphate and ammonium hydrogen phosphate.

In one example of the invention, the pharmaceutical composition is in the form of eye drop or an injectable hydrogel.

In one example of the invention, the therapeutic agent is a glaucoma drug at an appropriate dose, such as the dose ranging from 50 µg/ml to 500 µg/m.

In one yet further aspect, the invention provides a process for preparing the pharmaceutical composition of the invention, comprising the steps of:
(a) dissolving chitosan and gelatin in a solvent to obtain a mixture;
(b) adding a phosphate salt to the mixture obtained from step (a); and
(c) adding a therapeutic agent into the mixture as obtained in step (b).

In one more further aspect, the invention provides a method of delivering a therapeutic agent through mucous membrane in a subject, comprising:
(1) providing a pharmaceutical composition comprising the therapeutic agent in association with a chitosan, a gelatin, and a phosphate salt in a solvent at the ratio effective to provide a sustained-release or maintenance of the therapeutic agent in the location to be treated, wherein the phosphate salt is selected from the group consisting of disodium phosphate and ammonium hydrogen phosphate; and
(2) applying the pharmaceutical composition to the subject by oral administration, topical administration, intravenous injection, intracardiac injection, intramuscular injection, intraosseous injection, intraperitoneal injection, intradermal injection, subcutaneous injection, intraocular injection, intracavernous injection, or intra-articular injection;
whereby the therapeutic agent is sustained released or maintains in mucous membrane in the subject.

It is believed that a person of ordinary knowledge in the art where the present invention belongs can utilize the present invention to its broadest scope based on the descriptions herein with no need of further illustration. Therefore, the following descriptions should be understood as of demonstrative purpose instead of limitative in any way to the scope of the present invention.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIGS. 1A-1B show drug releasing characteristics in hydrogel under varies of circumstances.

FIGS. 3A-3B shows the IOP lowing effects of latanoprost-loaded hydrogel, wherein the ocular hypertension was induced by triamcinolone acetonide (TA) at day 0 and 7, the single subconjunctival injection of latanoprost-loaded hydrogel was performed at day 21, and the normal eyes (without treatment) were served as a control.

FIGS. 4A-4C provides the results of the administration of latanoprost-loaded hydrogel.

FIGS. 5A-5B shows the results of in-vivo agents release.

FIGS. 7A-7D show the IOPs of the animal groups treated with different formulations.

DETAILED DESCRIPTION OF THE INVENTION

Unless otherwise defined, all technical and scientific terms used herein have the same meaning as commonly understood by one of ordinary skill in the art to which this invention pertains. In the case of conflict, the present document, including definitions will control.

As used herein, the singular forms "a", "an", and "the" include plural referents unless the context clearly dictates otherwise. Thus, for example, reference to "a sample" includes a plurality of such samples and equivalents thereof known to those skilled in the art.

As used herein, the term "subject" refer to a human or a non-human mammal, such as a patient, a companion animal (e.g., dog, cat, and the like), a farm animal (e.g., cow, sheep, pig, horse, and the like) or a laboratory animal (e.g., rat, mouse, rabbit, and the like).

As used herein, the term "therapeutic agent" refers to an agent capable of inducing a biological effect in vivo and/or in vitro, including, but not limited to, a drug, an antibiotic agent, an anti-metabolic agent, a hormonal agent, a plant-derived agent, cells, stem cells, a vector carrying generic material, a peptide or a nucleic acid. The biological effect may be useful for treating and/or preventing a condition, disorder, or disease in a subject or patient.

As used herein, the term "mucous membrane" refers to the membrane linings of mostly endodermal origin, covered in epithelium, which are involved in absorption and secretion, such as those in nasal, oral, pharyngeal or urogenital regions.

The term "glaucoma drug" as used herein refers to a therapeutic agent, including a chemical or non-chemical molecule or a mixture or composition that provides an effect in the prevention or treatment of glaucoma. In some examples of the invention, the glaucoma drug is selected from the group consisting of prostaglandin, latanoprost, bimatoprost, travaprost, isopropyl unoprostone, timolol, brimonidine, iopidine, dorzolamide, brinzolamide, and combination thereof.

The term "sustained release" or "sustained releasing" as used herein refer to a release of a therapeutic agent in order to maintain a constant concentration for a specific period of time.

The term "sustained maintenance" or "sustained maintaining" as used herein refer to the maintenance of a therapeutic agent at a constant concentration for a specific period of time in a location to be treated.

The present invention provides a pharmaceutical composition comprising a therapeutic agent, a chitosan, a gelatin, and a phosphate salt in a solvent at the ratio effective to provide a sustained-release or maintenance of the therapeutic agent in the location to be treated in a subject.

Any phosphate salt may be used in the invention, particularly an inorganic phosphate salt. In some examples of the invention, the phosphate salt is selected from the group consisting of disodium phosphate and ammonium hydrogen phosphate. One particular example is disodium phosphate.

In the present invention, any solvent that co-dissolves the therapeutic agent, chitosan, gelatin and phospuate salt resulting in a solution can be used to provide the pharmaceutical composition of the invention. The solvent may be selected from the group consisting of dimethyl sulfoxide (DMSO), ethanol, glycerol, glycerol phosphate disodium, polyvinylpyrrolidone (MW 40000), polyvinylpyrrolidone (MW 36000), acetic acid, lactic acid and combination thereof. In one specific example, the solvent is glycerol.

According to the invention, the pharmaceutical composition may be prepared by the process comprising the steps of:
(a) dissolving chitosan and gelatin in a solvent to obtain a mixture;
(b) adding a phosphate salt to the mixture obtained from step (a); and
(c) adding a therapeutic agent into the mixture as obtained in step (b).

In the invention, the pharmaceutical composition may be prepared in the form of an injectable hydrogel, spray, drop, ointment, and suppository.

It has been proved in the invention that the pharmaceutical composition provides an unexpected effect in sustained release or maintenance of the therapeutic agent if associated with a formulation containing a chitosan, a gelatin, and a phosphate salt. As shown in the examples provided below, the therapeutic agent associated with the formulation maintained at a constant level in the location to be treated for at least 7 days, but not in the control, such as the results shown in FIGS. 7A-7C.

According to the invention, the pharmaceutical composition may be applied by oral administration, topical administration, intravenous injection, intracardiac injection, intramuscular injection, intraosseous injection, intraperitoneal injection, intradermal injection, subcutaneous injection, intraocular injection, intracavernous injection, and intra-articular injection. In one specific example, the intraocular injection comprising subconjunctval injection, intravitreal injection, or transscleral injection.

Accordingly, the invention provides a method of delivering a therapeutic agent through mucous membrane in a subject, comprising:
(1) providing a pharmaceutical composition comprising the therapeutic agent in association with a chitosan, a gelatin, and a phosphate salt in a solvent at the ratio effective to provide a sustained-release or maintenance of the therapeutic agent in the location to be treated, wherein the phosphate salt is selected from the group consisting of disodium phosphate and ammonium hydrogen phosphate; and
(2) applying the pharmaceutical composition to the subject by oral administration, topical administration, intravenous injection, intracardiac injection, intramuscular injection, intraosseous injection, intraperitoneal injection, intradermal injection, subcutaneous injection, intraocular injection, intracavernous injection, or intra-articular injection;
whereby the therapeutic agent is sustained released or maintains in mucous membrane in the subject.

On the other hand, the invention provides an injectable hydrogen formulation for the administration of a therapeutic agent to a mucous membrane, for the administration of a therapeutic agent to a mucous membrane, which provides a sustained-release or maintenance of the therapeutic agent in the location to be treated in a subject. which provides a sustained-release or maintenance of the therapeutic agent in the location to be treated in a subject. The pharmaceutical composition of the invention may be applied by oral administration, topical administration, intravenous injection, intracardiac injection, intramuscular injection, intraosseous injection, intraperitoneal injection, intradermal injection, subcutaneous injection, intraocular injection, intracavernous injection, and intra-articular injection. The intraocular injection includes but is not limited to subconjunctival injection, intravitreal injection, or transscleral injection.

In particular, the invention provides a pharmaceutical composition for treatment or prevention of a disease in eyes, comprising a therapeutic agent, a chitosan, a gelatin, and a phosphate salt in a solvent at the ratio effective to provide a sustained-release or maintenance of the therapeutic agent, wherein the phosphate salt is selected from the group consisting of disodium phosphate and ammonium hydrogen phosphate. The pharmaceutical composition may be in the form of eye drop or an injectable hydrogel.

In one example, the therapeutic agent is a glaucoma drug. The pharmaceutical composition contains a glaucoma drug at the dose ranging from 50 μg/ml to 500 μg/ml.

Some examples below are provided to be construed as merely illustrative, and not limitative of the remainder of the disclosure in any way whatsoever. Without further elaboration, it is believed that one skilled in the art can, based on the description herein, utilize the present invention to its fullest extent.

Example

1. Preparation of Hydrogel Mixed with a Glaucoma Agent

A combination of 2% chitosan (degree of deacetylation >95%, Xing Cheng Biochemical Factory Nantong, China) with 0.2% gelatin (G2500, Sigma, USA) was dissolved in 0.1 M acetic acid (242853, Sigma, USA) and sterilized by autoclave. A 10% (w/v) disodium phosphate (S7907, Sigma, USA) and glycerol (G7893, Sigma, USA) solution was sterilized by filtration. The disodium phosphate and glycerol solution was added dropwise into the chitosan/gelatin solution under stirring, and the pH value was adjusted to 7.4. The mixture solution was stored at 4° C. and utilized as a sustained release/maintenance system of latanoprost. Latanoprost (L1167, Sigma, USA) was added into the mixture solution under stirring and cooling in an ice-water bath for 30 minutes. Then, 500 μg/ml of latanoprost-loaded hydrogel was prepared under a laminar flow hood and stored at 4° C. until further use.

2. Preparation of Oral Gel Mixed with Agents

Chitosan (degree of deacetylation >95%) was purchased from Xing Cheng Biochemical Factory Nantong, China. Lactic acid, acetic acid, sodium hydroxide, polyvinylpyrrolidone (MW 40000) and 0.1% polyvinylpyrrolidone (MW 36000) and latanoprsot were purchased from Sigma-Aldrich.

The 1% lactic acid and 0.1% acetic acid were mixed, and the pH value was adjusted to 4.5 by adding 3N NaOH. The concentration of chitosan to reach optimal drug-releasing curve was determined from 0.15% to 0.5% chitosan. The 1% gelatin, 1% polyvinylpyrrolidone (MW 40000) and 0.1% polyvinylpyrrolidone (MW 36000) were added to enhance the viscosity of mixture solution. Then, an agent can be added into the mixture and measured the sustained-release characteristics of the agent.

3. Physical Characteristics of Hydrogel

Viscosity measurements were performed using a TA Instruments HR-1 rheometer equipped with a Peltier plate (Aluminum, 20-mm plate) in oscillatory mode (TA Instruments, New Castle, Del.). The viscosity of hydrogel and latanoprost-loaded hydrogel were measured at a gap of 1 mm and a fixed frequency of 1.0 Hz. In the gelation temperature analysis, the samples were measured at 25° C. All samples were prepared and tested in triplicate. The result was shown in Table 1.

TABLE 1

The viscosity of hydrogel and latanoprsot-loaded hydrogel.

| Group | Viscosity (cP) |
|---|---|
| Hydrogel | 276.11 ± 16.70 |
| Latanoprost-loaded hydrogel | 277.08 ± 19.51 |

4. Sterilization and Antiseptic by Filtration

In order to comply with safety and qualified by principles of biomedical and drug manufactures, the hydrogel was sterilized under high pressure (autoclave), moist heat (121° C. for 15 minutes or 134° C. for 3 minutes) and filtration.

5. In-Vitro Agents Release

In-vitro experiment on agent release of hydrogel is designed to simulate its in-vivo effect. The 500 μg/ml latanoprost-loaded solution were added to the transwell (100 μl/well) mounted on 24-well plates, and 1.5 ml PBS was added in each well and then incubated at 37° C. The 1.5 ml PBS was collected and another 1.5 ml PBS was then replenished at each time (Days 1, 7, 14 and 28). The amount of latanoprost was analyzed by a LC-MS/MS system equipped with an electrospray ionization source. The LC-MS/MS consisted of a Sciex API 3000 tandem mass spectrometer and Agilent 1100 series LC system. Separation of latanoprost was achieved by using a Phenomenex Luna C18 column (particle size 5 um, 50 mm×4.6 mm i.d.). The mobile phase consisted of latanoprost was (A) 0.1% (v/v) formic acid and (B) acetonitrile containing 0.1% formic acid (A:B=7:3, v/v) and delivered at 0.3 ml per minute. The mass spectrometer was operated in positive mode which used multiple reaction monitoring. The precursor to produce ion transition of m/z 374.2→195.2 was monitored. In another experiment, the dialysis bags with molecular weight cut-off of 1 kD were used to retain the diclofenac-loaded hydrogel and allow the released diclofenac to permeate into the release medium (PBS). Briefly, 800 μl diclofenac-loaded hydrogel (1 mg/ml) or diclofenac only (1 mg/ml) was added to a dialysis bag. The sample-loaded dialysis bag was immersed in 30 ml of PBS at 100 rpm and 37° C. At fixed time intervals, the release medium was collected and replaced with an equal amount of PBS. According to the absorption curve of diclofenac, the diclofenac content of the each sample was analyzed by Tecan's Infinite® M 1000 spectrophotometer at the wavelength of 300 nm.

Figure 1:
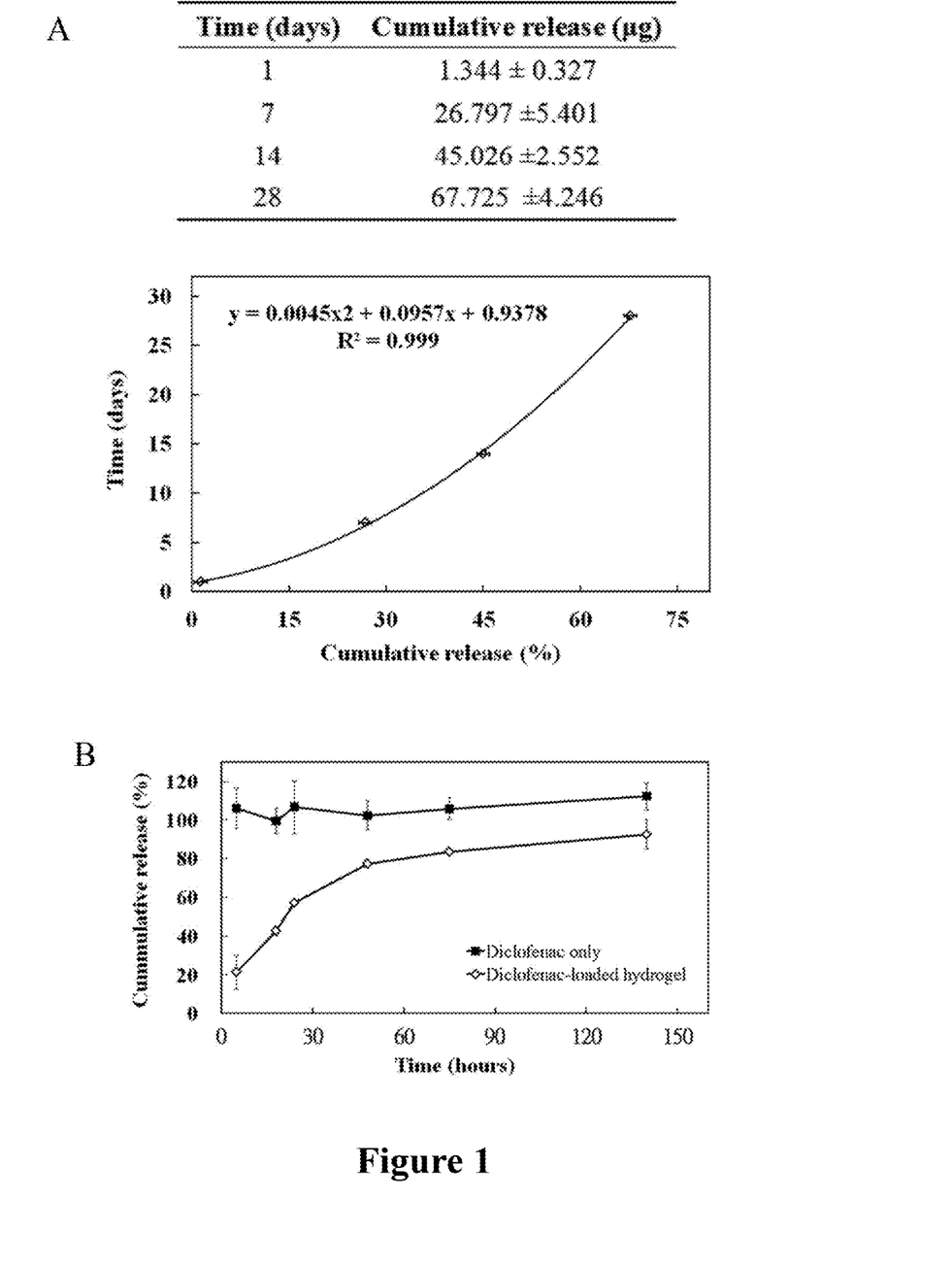
FIG. 1A shows the in-vitro release study with Mass spectrum at a positive ionization mode of latanoprost, and the cumulative percent release of latanoprost from hydrogels in PBS at 37° C. (n=5).
FIG. 1B shows the release of diclofenac which expressed as cumulative drug release (%) (n=5).

As showed in FIG. 1A, the release of latanoprost from the hydrogel was calculated from the linear standard curve of latanoprost and expressed as cumulative drug release (%). The percentage of cumulative release at 1, 7, 14 and 28 days were 1.34±0.33, 26.80±5.40, 45.03±2.55 and 67.72±4.25%, respectively. Additives in hydrogel affect its composition, structure and may also change its drug releasing characteristics. As shown in FIG. 1B, the percentage of cumulative release of 1 mg/ml diclofenac from hydrogels at 5, 18, 24, 48, 75 and 140 hours was 21.33±8.73, 42.50±2.19, 57.02±1.56, 77.33±2.18, 83.36±1.40 and 92.41±7.62%, respectively. The percentage of cumulative release of 1 mg/ml diclofenac only group at 5, 18, 24, 48, 75 and 140 hours was 106.08±10.48, 99.34±6.57, 106.62±13.76, 102.28±7.40, 105.75±5.76 and 112.14±7.05%.

6. Evaluation of Cytotoxicity of the Hydrogel

Figure 2:
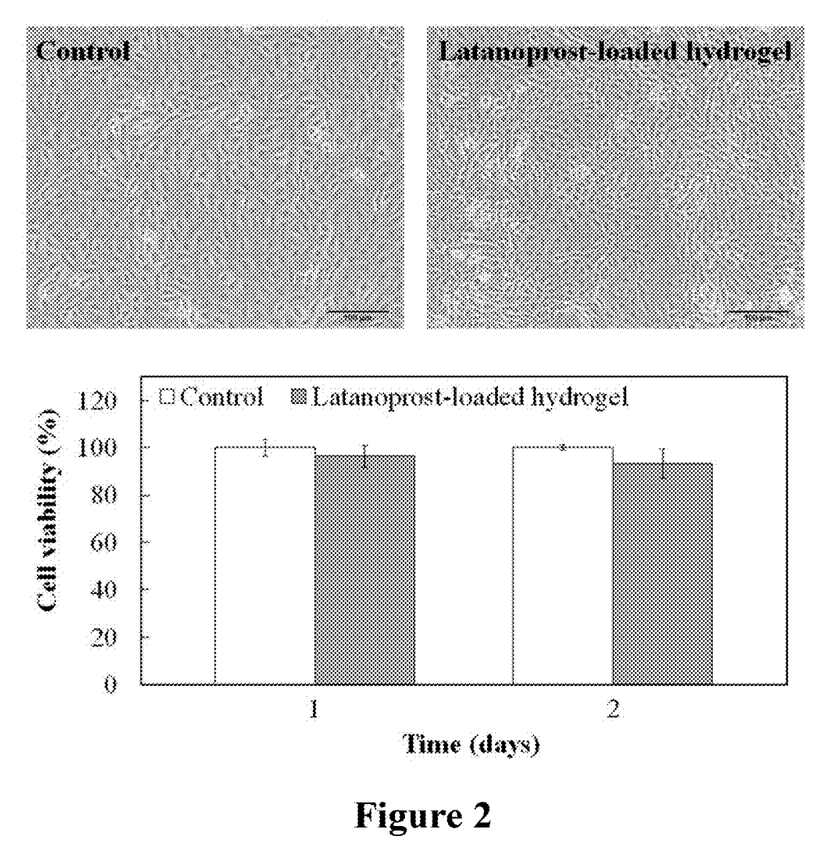
FIG. 2 shows the cytotoxicity of latanoprost-loaded hydrogels to HCEC, wherein the cell morphology is at day 2 (scale bar, 100 µm) and the crystal violet assay is at days 1 and 2 (n=4, p>0.05).

The cytotoxicity of hydrogel on human corneal epithelial cells (HCEC) was evaluated by crystal violet assay. Hydrogel (0.1 g) was immersed in 1 ml Dulbecco's Modified Eagle's Medium/Nutrient Mixture F-12 Ham (DMEM-F12, D8900, Sigma, USA) containing 5% fetal bovine serum (FBS, AXB30114, Hyclone, USA), 10 ng/ml epidermal growth factor (AF-100-15, PeproTech, USA) and 1% penicillin-streptomycin (15140-122, Gibco, USA) in a 48-well plate at 37° C., 5% carbon dioxide and 95% relative humidity for 72 hours to prepare the extraction medium for the cytotoxicity test. HCECs were seeded in the 96-well cell culture plates with the density of 5000 cells per well and cultured in DMEM-F12. After incubation for 18 hours, the cells were washed with phosphate-buffered solution (PBS); 200 μl hydrogel extractive solution was then added into the culture well as culture medium. Crystal violet (C3886, Sigma, USA) was dissolved in 10% (v/v) ethanol (E7148, Sigma, USA). On day 1 and day 2, the cells were washed with PBS, and 50 µl 0.2% (w/v) crystal solution was added into each culture well for 10 minutes. The crystal violet dye was carefully washed in running water, and then 100 µl 33% (v/v) acetic acid was added in the dry well. The absorbance was measured using an enzyme-linked immunosorbent assay (ELISA, Sunrise remote, TECAN, USA) reader at the wavelength of 570 nm. As shown in FIG. 2, the OD values of the control group at 24 and 48 hours were 1.192±0.042 and 1.635±0.018, respectively. The OD values of the latanoprost-loaded hydrogel group at 24 and 48 hours were 1.149±0.054 and 1.524±0.099, respectively. There was no significant difference in the OD values between the control and the latanoprost-loaded hydrogel group at 24 and 48 hours (n=4, p>0.05). The results showed no cytotoxic effects of latanoprost-loaded hydrogel on HCEC.

7 Subconjunctival Delivery of Latanoprost-Loaded Hydrogel

Figure 3:
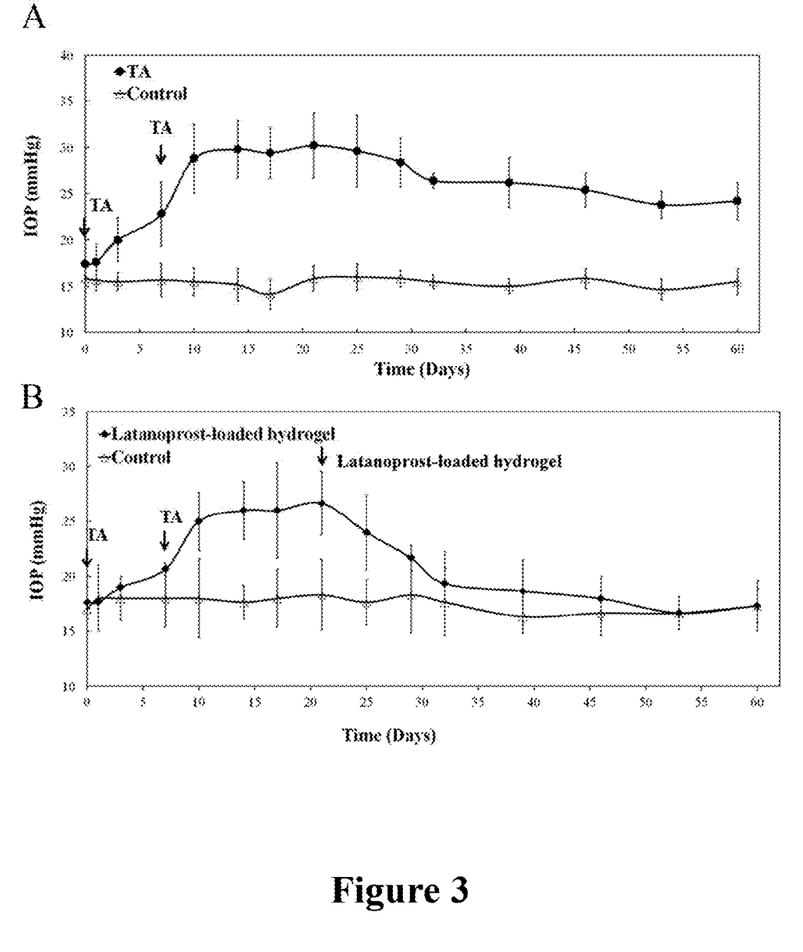
FIG. 3A shows that the IOP was increased after the intravitreal injection of TA.
FIG. 3B shows that the IOP was decreased in the post-treatment of latanoprost-loaded hydrogel (n=3, *p<0.05).

The animal experiment was approved by the Ethics Committee for Animal Research of the Taipei Veterans General Hospital, Taipei, Taiwan. Ten male New Zealand albino rabbits with body weight approximately 2 kg were used and maintained in accordance with the guidelines for the care and use of laboratory animals. All procedures were performed under general anesthesia with of 10 mg/kg of tiletamine and zolazepam (Zoletil 50, Virbac, France) and topical anesthesia (0.5% of proparacaine hydrochloride). Ocular hypertension was induced by triamcinolone acetonide (TA). Each rabbit was treated by an intravitreal injection of 0.1 ml TA (4% of triamcinolone suspended Inj., Tai-yu Company, Taiwan) in the right eye at day 0 and 7. IOP measurement was performed with an Icare® TONOLAB tonometer for laboratory research (TonoLab, Tiolat, Helsinki, Finland) at Days 0 (pre-injection), 1, 3, 7, 10, 14, 17 and 21. After day 7, the IOP of the right eye was significantly elevated as compared with the left eye (control group). At day 21, 100 µl latanoprost-loaded hydrogel was injected into subconjunctival space of lower lid of the right eye using a 30-gauge needle. The IOP was then recorded at day 25, 29, 32, 39, 46, 53 and 60. As shown in FIG. 3A, the mean IOP was significantly higher in the eyes that received an intravitreal injection of TA compared with that in the control eyes. The IOP elevation was first noted 3 days after injection and remained elevated until 60 days after the first TA injection. A series of IOP measurements after the injection of latanoprost-loaded hydrogel were plotted for efficacy analysis (FIG. 3B). Latanoprost-loaded hydrogel was injected into the subconjunctival space of the lower lid of the right eye at day 21. The mean IOP reduction was 2.4 mmHg (9.2%) at day 25. There was no significant difference in the mean IOP between the latanoprost-loaded hydrogel group and the control group after day 29.

8 In-Vivo Biocompatibility of Latanoprost-Loaded Hydrogel

Figure 4:
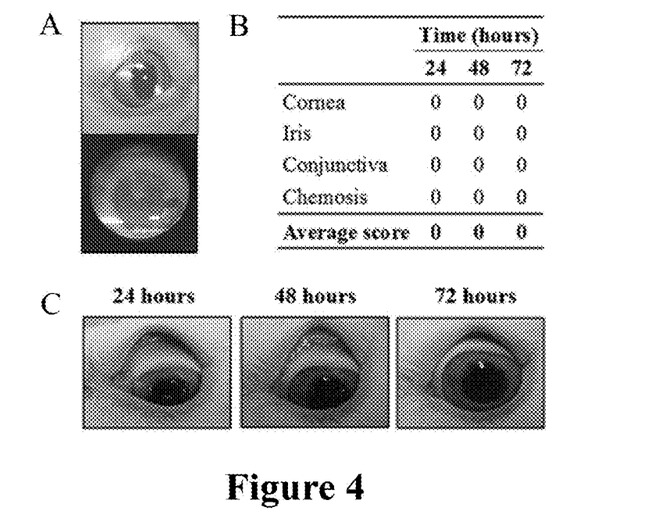
FIG. 4A shows the image of the portable slit-lamp examination for corneal and anterior chamber.
FIG. 4B provides the readings of Draize score.
FIG. 4C provides an image of the observation of external rabbit's eye were performed at 24, 48 and 72 hours (n=5).

The protocol of the ocular irritation test was approved by the Ethics Committee for Animal Research of the Taipei Veterans General Hospital, Taipei, Taiwan. Three female New Zealand albino rabbits with body weight approximately 2.5 kg were used and maintained in accordance with the guidelines for the care and use of laboratory animals. One hundred microliters of latanoprost-loaded solution was instilled into one of the eyes, while the other eye was used as control. Tolerability of latanoprost-loaded hydrogel was evaluated by Draize rabbit eye irritation test. According to the Draize scale, the opacity (cornea), swelling (iris), discharge (conjunctiva) and chemosis were graded on a scale from 0 to 4, 0 to 2, 0 to 3, and 0 to 4, respectively. Readings were performed at 24, 48 and 72 hours after the administration. As shown in FIG. 4A-4C, during the 3-day observation period, no abnormal clinical signs associated with latanoprost-loaded hydrogel were noted in the cornea, iris, and conjunctiva (including discharge and chemosis).

9 In-Vivo Release Study

The protocol of the ocular irritation test was approved by the Ethics Committee for Animal Research of the Taipei Veterans General Hospital, Taipei, Taiwan. The concentration of latanoprost in aqueous humor was analyzed by LC-MS/MS system. Three male New Zealand albino rabbits with body weight approximately 2 kg were used and maintained in accordance with the guidelines for the care and use of laboratory animals. The rabbits were anesthetized with 10 mg/kg of tiletamine and zolazepam (Zoletil 50, Virbac, France) and topical anesthesia (0.5% proparacaine hydrochloride). One hundred microliter of latanoprost-loaded hydrogel was injected into subconjunctival space of lower lid of the right eye using a 30-gauge needle. Briefly, 100 µl aqueous humor from each eye were aspirated using a 30-gauge needle at day 3, 5, 7, 17 and 27. The samples were added to 300 µl of acetonitrile and then stored at 4° C. until analysis. In another experiment, the rats were anesthetized by intraperitoneal injection of of tiletamine and zolazepam (Zoletil 50, Virbac, France), and prepared sterile for dorsal injections. Fluorescein isothiocyanate-conjugated bovine serum albumin (FITC-BSA)-loaded hydrogel (2 mg/ml) was injected into the subcutaneous space. Each injection was 0.2 ml in volume. Animals were sacrificed by $CO_2$ asphyxiation, and the direct observations of fluorescence were performed by UV lamp at days 3 and 7.

Figure 5:
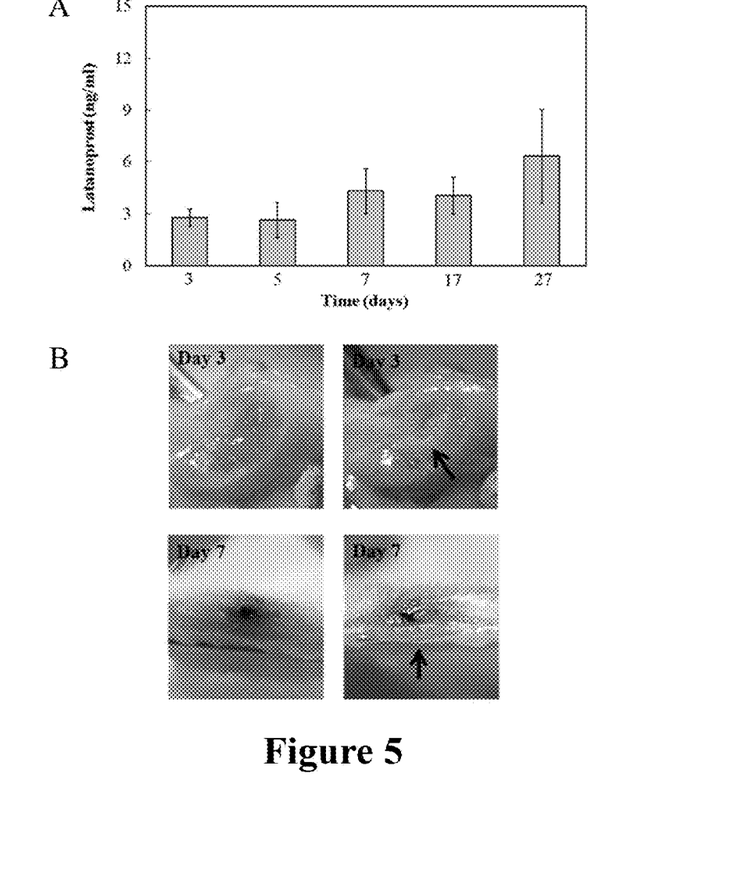
FIG. 5A shows the aqueous humor levels of latanoprost in rabbits after administration of latanoprost-loaded hydrogel at 3, 5, 7, 17 and 27 days (n=3).
FIG. 5B shows the result of fluorescence after subcutaneous administration of fluorescein isothiocyanate-conjugated bovine serum albumin (FITC-BSA) hydrogel to rats.

After the administration of latanoprost-loaded hydrogel, the concentration of latanoprost in the aqueous humor at 3, 5, 7, 17 and 27 days was 2.77±0.50, 2.64±1.02, 4.30±1.30, 4.04±1.06 and 6.32±2.70 ng/ml, respectively (FIG. 5A). The FIG. 5B shows the positive fluorescence results of FITC-BSA release were observed at days 3 and 7.

10 Hemolysis Analysis of Latanoprost-Loaded Hydrogel

Hemolytic activity of the latanoprost-loaded hydrogel was tested by direct and indirect contact methods. Diluted pooled rabbit blood (1 ml) with a total hemoglobin concentration of 10±1 mg/ml was mixed with 7 ml of extract extracted from the control or test articles. The positive control is Buna-N rubber with a thickness of 0.8 mm and the extraction ratio was 21 $cm^2$:7 ml. The negative control is high density polyethylene film with a thickness of <0.5 mm and the extraction ratio was 42 $cm^2$:7 ml. The extraction ratio of the test article (500 ug/ml of latanoprost-loaded hydrogel) was 1.4 g: 7 ml. The tubes were gently mixed and incubated at 37° C. for 3 hours. After incubation, the suspension was centrifuged at 700×g for 15 min, and the absorbance of the supernatant of each tube was measured by the ELISA reader at the wavelength of 540 nm. The percentage of hemolysis was calculated according to the following equation:

$$\text{Hemolysis}(\%) = \frac{\text{Supernatant hemoglobin concentration} \times 100\%}{\text{Total hemoglobin concentration in tube}}$$

Figure 6:
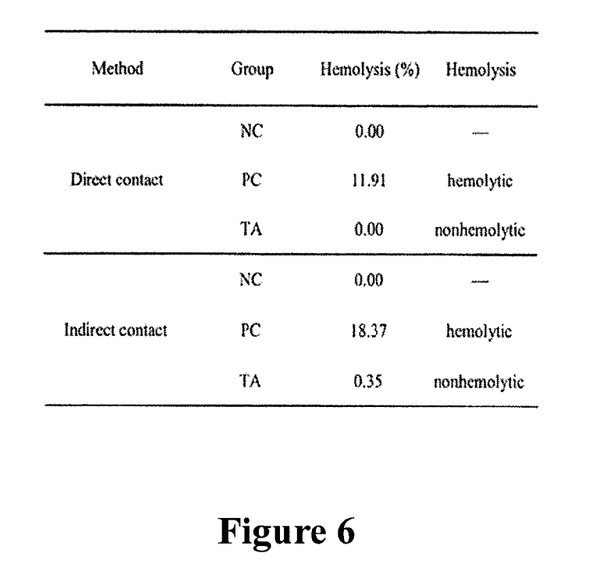
FIG. 6 shows the hemolytic activity of the latanoprost-loaded hydrogel which tested by direct and indirect contact methods, wherein the NC which means negative control (high-density polyethylene film); the PC which means positive control (Buna-N rubber); and the TA which means test article.

The results as showed in FIG. 6.

11 Topical Administration of Latanoprost-Loaded Hydrogel

Figure 7:
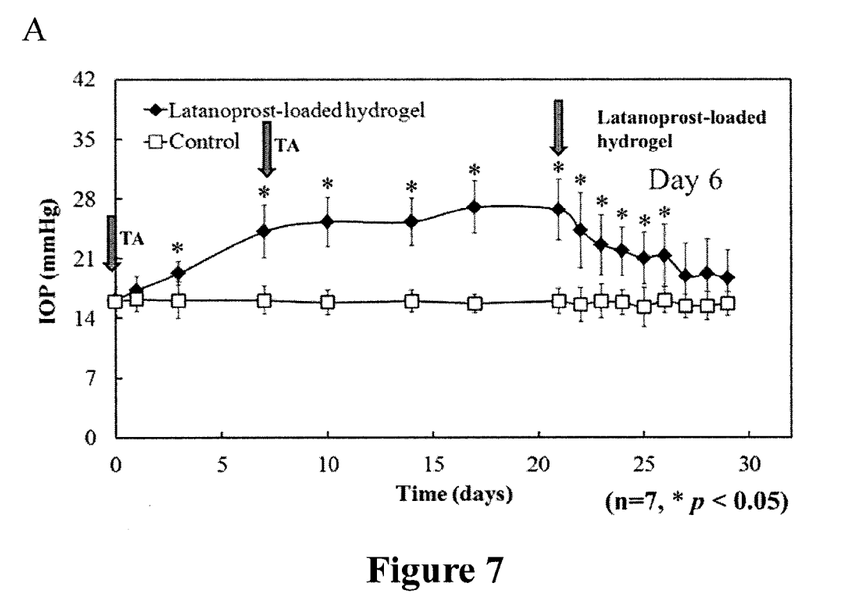
FIG. 7A shows the IOP of the latanoprost-loaded hydrogel according to the invention, wherein the ocular hypertension was induced by triamcinolone acetonide (TA) at day 0 and 7 and single topical administration of latanoprost-loaded hydrogel was performed at day 21, and the normal eyes (without treatment) were served as a control.
FIG. 7B shows the ocular hypertension induced by TA at day 0 and 7, wherein the single topical administration of hydrogel was performed at day 21, and the normal eyes (without treatment) were served as a control.
FIG. 7C shows the ocular hypertension induced by TA at day 0 and 7, wherein the single topical administration of latanoprost-loaded hydrogel or XALATAN® was performed at day 21.
FIG. 7D shows the effects of repeat dose administration of latanoprost-loaded hydrogel. The ocular hypertension induced by TA at day 0, 3 and 5, wherein the topical administrations of latanoprost-loaded hydrogel were performed at day 7 and 14. The IOP was increased after the intravitreal injection of TA and then decreased in the post-treatment of latanoprost-loaded hydrogel (n=3). The normal eyes (without treatment) were served as a control.

The animal experiment was approved by the Ethics Committee for Animal Research of the Taipei Veterans General Hospital, Taipei, Taiwan. New Zealand albino rabbits (body weight approximately 2 kg) were used and maintained in accordance with the guidelines for the care and use of laboratory animals. All procedures were performed under general anesthesia with 10 mg/kg tiletamine and zolazepam (Zoletil 50, Virbac, France) and topical anesthesia (0.5% of proparacaine hydrochloride). Ocular hypertension was induced by triamcinolone acetonide (TA). Each rabbit was treated by an intravitreal injection of 0.1 ml TA (4% of triamcinolone suspended Inj., Tai-yu Company, Taiwan) in the right eye at days 0 and 7. IOP measurement was performed with an Icare® TONOLAB tonometer for laboratory research (TonoLab, Tiolat, Helsinki, Finland) at days 0 (pre-injection), 1, 3, 7, 10, 14, 17 and 21. After day 7, the IOP of the right eye was significantly elevated compared with the left eye (control group). At day 21, the rabbits were divided into two groups randomly. 50 µl of latanoprost-loaded hydrogel (FIG. 7A), hydrogel (FIG. 7B) or XALATAN® (latanoprost) (FIG. 7C) were instilled into lower lid of the right eye. The IOP was then recorded. The effects of the repeat dose administration of latanoprost-loaded hydrogel were also evaluated by TA-induced high IOP models. Each rabbit was treated by an intravitreal injection of 0.1 ml TA in the right eye at days 0, 3 and 5. IOP measurement was performed with an Icare® TONOLAB tonometer at days 0 (pre-injection), 1, 2, 3, 4, 5, 6 and 7. At day 7, the IOP of the right eye was significantly elevated compared with the left eye (control group) and then 250 µ/ml of latanoprost-loaded hydrogel (50 µl) were instilled into lower lid of the right eye (FIG. 7D). The IOP was then recorded.

As shown in FIG. 7A, the IOP was increased after the intravitreal injection of TA and then decreased in the post-treatment of latanoprost-loaded hydrogel (n=7, *p<0.05). As shown in FIG. 7B, the IOP was increased after the intravitreal injection of TA. After administration of hydrogel, the mean IOP was significantly higher than that in control group (n=3, *p<0.05). As shown in FIG. 7C, the IOP was increased after the intravitreal injection of TA and then decreased in the post-treatment of latanoprost-loaded hydrogel or XALATAN ( ). There were no significant difference between latanoprost-loaded hydrogel and XALATAN group (n=5, *p<0.05). As shown in FIG. 7D, the IOP was increased after the intravitreal injection of TA and then decreased in the post-treatment of latanoprost-loaded hydrogel (n=3).

12 In-Vivo Release with Topical Administration of Latanoprost-Loaded Hydrogel The concentration of latanoprost in aqueous humor was analyzed by an LC-MS/MS system. Three male New Zealand albino rabbits (body weight approximately 2 kg) were used and maintained in accordance with the guidelines for the care and use of laboratory animals. The rabbits were anesthetized with 10 mg/kg tiletamine and zolazepam (Zoletil 50, Virbac, France) and topical anesthesia (0.5% proparacaine hydrochloride). Latanoprost-loaded hydrogel (50 µl) was instilled into lower lid of the right eye. Briefly, 100 µl aqueous humor from each eye was aspirated using a 30-gauge needle on days 1, 2, 3, 4, 5, 6 and 7. The samples were added to 300 µl of acetonitrile and then stored at 4° C. until analysis.

Figure 8:
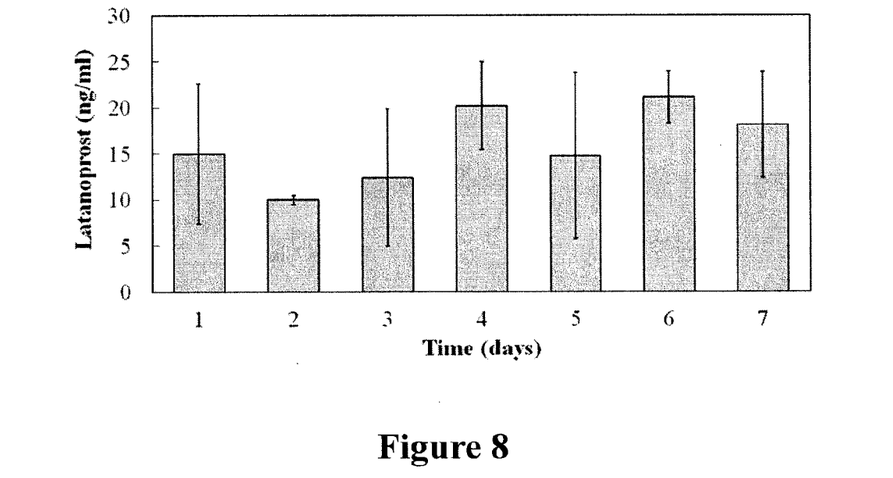
FIG. 8 shows the aqueous humor levels of latanoprost in rabbits after the single topical administration of latanoprost-loaded hydrogel at 1, 2, 3, 4, 5, 6 and 7 days (n=3).

After the administration of latanoprost-loaded hydrogel, the concentration of latanoprost in the aqueous humor at 1, 2, 3, 4, 5, 6 and 7 days was 15.01±7.60, 9.98±0.51, 12.41±7.47, 20.20±4.76, 14.77±9.05, 21.11±2.81 and 18.12±5.78 ng/ml, respectively (FIG. 8).

While this invention has been disclosed with reference to specific embodiments, it is apparent that other embodiments and variations of this invention may be devised by others skilled in the art without departing from the true spirit and scope of the invention.

We claim:

1. A pharmaceutical composition comprising a therapeutic agent, a chitosan, a gelatin, and disodium phosphate in a solvent at the ratio effective to provide a sustained-release or maintenance of the therapeutic agent in the location to be treated in a subject, wherein said composition is formulated in the form of an eye drop.

2. The pharmaceutical composition of claim 1, wherein the solvent is selected from the group consisting of dimethyl sulfoxide (DMSO), ethanol, glycerol, polyvinylpyrrolidone (MW 40000), polyvinylpyrrolidone (MW 36000), acetic acid, lactic acid and a combination thereof.

3. The pharmaceutical composition of claim 1, wherein the solvent is glycerol.

4. The pharmaceutical composition of claim 1, wherein the therapeutic agent is selected from the group consisting of a drug, an antibiotic agent, an anti-metabolic agent, an hormonal agent, a plant-derived agent, cells, stem cells, and a peptide.

5. The pharmaceutical composition of claim 1, which is applied by topical administration.

6. A pharmaceutical composition for treatment of a disease in eyes, comprising a therapeutic agent, a chitosan, a gelatin, and disodium phosphate in a solvent at the ratio effective to provide a sustained-release or maintenance of the therapeutic agent, wherein said composition is formulated in the form of an eye drop.

7. The pharmaceutical composition for treatment of a disease in eyes of claim 6, wherein the solvent is selected from the group consisting of dimethyl sulfoxide (DMSO), ethanol, glycerol, glycerol phosphate disodium, polyvinylpyrrolidone (MW 40000), polyvinylpyrrolidone (MW 36000), acetic acid, lactic acid and a combination thereof.

8. The pharmaceutical composition for treatment of a disease in eyes of claim 7, wherein the solvent is glycerol.

9. The pharmaceutical composition for treatment of a disease in eyes of claim 6, wherein the therapeutic agent is a glaucoma drug.

10. The pharmaceutical composition for treatment of a disease in eyes of claim 9, which contains the glaucoma drug at the dose ranging from 50 µg/ml to 500 µg/ml.

11. The pharmaceutical composition for treatment of a disease in eyes of claim 9, wherein the glaucoma drug is selected from the group consisting of prostaglandin, latanoprost, bimatoprost, travaprost, isopropyl unoprostone, timolol, brimonidine, iopidine, dorzolamide, brinzolamide, and a combination thereof.

12. The pharmaceutical composition for treatment of a disease in eyes of claim 9, wherein the glaucoma drug is prostaglandin.

13. A process for preparing the pharmaceutical composition of claim 1, comprising the steps of:

(a) dissolving chitosan and gelatin in a solvent to obtain a mixture;
(b) adding disodium phosphate to the mixture obtained from step (a); and (c) adding a therapeutic agent into the mixture as obtained in step (b).

14. The process of claim 13, wherein the solvent is selected from the group consisting of dimethyl sulfoxide (DMSO), ethanol, glycerol, glycerol phosphate disodium, polyvinylpyrrolidone (MW 40000), polyvinylpyrrolidone (MW 36000), acetic acid, lactic acid and a combination thereof.

15. The process of claim 14, wherein the solvent is glycerol.

16. A method of delivering a therapeutic agent through a mucous membrane in a subject, comprising:
(a) providing the pharmaceutical composition of claim 1; and
(b) applying the pharmaceutical composition to the subject by topical administration.

\* \* \* \* \*